United States Patent
Zhu et al.

(10) Patent No.: US 7,285,160 B2
(45) Date of Patent: Oct. 23, 2007

(54) INK JET INK COMPOSITION FOR WETNESS INDICATION

(75) Inventors: Linfang Zhu, Naperville, IL (US); James D. McClellan, Mt. Prospect, IL (US); John P. Folkers, Arlington Heights, IL (US)

(73) Assignee: Videojet Technologies Inc., Wood Dale, IL (US)

( * ) Notice: Subject to any disclaimer, the term of this patent is extended or adjusted under 35 U.S.C. 154(b) by 0 days.

(21) Appl. No.: 10/701,733

(22) Filed: Nov. 4, 2003

(65) Prior Publication Data

US 2005/0092204 A1    May 5, 2005

(51) Int. Cl.
*C09D 11/00* (2006.01)
*G01D 11/00* (2006.01)

(52) U.S. Cl. ............... 106/31.58; 106/31.59; 106/31.43; 347/100

(58) Field of Classification Search ....... 106/31.58, 106/31.59, 31.43; 347/100
See application file for complete search history.

(56) References Cited

U.S. PATENT DOCUMENTS

| | | | |
|---|---|---|---|
| 3,675,654 A | | 7/1972 | Baker et al. |
| 4,022,211 A | | 5/1977 | Timmons et al. |
| 4,136,076 A | | 1/1979 | Daniels |
| 4,153,467 A | * | 5/1979 | Yano et al. .......... 347/100 |
| 4,179,397 A | | 12/1979 | Rohowetz et al. |
| 4,465,800 A | | 8/1984 | Bhatia |
| 4,909,879 A | | 3/1990 | Ball |
| 5,075,699 A | | 12/1991 | Koike et al. |
| 5,102,458 A | * | 4/1992 | Lent et al. .......... 106/31.43 |
| 5,167,703 A | | 12/1992 | Eida et al. |
| 5,197,958 A | | 3/1993 | Howell |
| 5,211,747 A | | 5/1993 | Breton et al. |
| 5,257,036 A | | 10/1993 | Koike et al. |
| 5,389,093 A | | 2/1995 | Howell |
| 5,560,770 A | * | 10/1996 | Yatake .......... 106/31.43 |
| 5,661,511 A | * | 8/1997 | Kashiwazaki et al. ...... 347/100 |
| 5,686,508 A | | 11/1997 | Shimomura et al. |
| 5,702,377 A | | 12/1997 | Collier, IV et al. |
| 5,710,195 A | | 1/1998 | Subbaraman et al. |
| 5,952,401 A | | 9/1999 | Kimura et al. |
| 5,973,025 A | | 10/1999 | Nigam et al. |
| 5,985,975 A | | 11/1999 | Kurabayashi et al. |
| 6,383,274 B1 | * | 5/2002 | Lin .......... 106/31.27 |
| 6,506,240 B2 | * | 1/2003 | Takemoto et al. ....... 106/31.36 |
| 2003/0207091 A1 | * | 11/2003 | Nair et al. .............. 428/195.1 |

FOREIGN PATENT DOCUMENTS

| | | |
|---|---|---|
| EP | 0 314 403 A | 5/1989 |
| GB | 2055393 A | 3/1981 |
| JP | 55145774 A2 | 11/1980 |
| JP | 55161873 A | 12/1980 |
| JP | 56088473 A | 7/1981 |
| JP | 56090865 A | 7/1981 |
| JP | 57006789 A | 1/1982 |
| JP | 58141260 A | 8/1983 |
| JP | 61 106679 A | 5/1986 |
| JP | 62004763 A | 1/1987 |
| JP | 62035850 A2 | 2/1987 |
| JP | 63090582 A2 | 4/1988 |
| JP | 63213582 A | 9/1988 |
| JP | 63312881 A2 | 12/1988 |
| JP | 01 042286 A | 2/1989 |
| JP | 01118583 A | 5/1989 |
| JP | 01135880 A | 5/1989 |
| JP | 1263169 A2 | 10/1989 |
| JP | 2014262 A2 | 1/1990 |
| JP | 03 277671 A | 12/1991 |
| JP | 4202573 A2 | 7/1992 |
| JP | 7062284 A2 | 3/1995 |
| JP | 9324146 A2 | 12/1997 |
| WO | WO 86/04219 | 7/1986 |
| WO | WO 94/10958 | 5/1994 |

OTHER PUBLICATIONS

Search Results—ink jet ink /methanol/ water soluble dye / resin from USPTO website, Jun. 9, 2003, 2 pages.
Search Results—ink jet / methanol from USPTO website, Jun. 9, 2003, 2 pages.
Search Results—ink jet / methyl alcohol from USPTO website, Jun. 11, 2003, 2 pages.

* cited by examiner

*Primary Examiner*—Melissa Koslow
*Assistant Examiner*—Veronica Faison-Gee
(74) *Attorney, Agent, or Firm*—Leydig, Voit & Mayer, Ltd

(57) ABSTRACT

Disclosed is an ink composition which is suitable for ink jet printing and comprising an organic solvent, for example, methanol, a water-soluble resin, a water-soluble dye, and optionally a surfactant, wherein, if water is present, it is present in an amount less than 50% by weight of the ink composition. The ink composition is suitable for printing messages on substrates such as diaper outer liner fabrics. The printed messages are removed upon contact with water or urine or other aqueous body fluid, thereby providing an indication of diaper wetness.

29 Claims, No Drawings

INK JET INK COMPOSITION FOR WETNESS INDICATION

FIELD OF THE INVENTION

This invention pertains to ink jet ink compositions in general, and in particular, to ink jet ink compositions suitable for printing marks or messages on substrates such as diapers. Such marks, when contacted with an aqueous body fluid such as urine, undergo a change in appearance to indicate wetness.

BACKGROUND OF THE INVENTION

Methods have been proposed to indicate wetness in a diaper. For example, the inner surface (or the surface towards the body) of the outer liner of the diaper may have a printed message such as animal figures, alphabets, or other patterns attractive to infants. When the diaper becomes wet and the urine reaches the outer liner, the figure or pattern in the printed message will dissolve or otherwise become smudged. Such smudging will be visible to observers, thereby indicating that a diaper change is required.

Ink jet printing has been proposed for printing messages on the diaper outer liner. Ink jet printing is a well-known technique by which printing is accomplished without contact between the printing device and the substrate on which the printed characters are deposited. Briefly described, ink jet printing involves the technique of projecting a stream of ink droplets to a surface and controlling the direction of the stream so that the droplets are caused to form the desired printed image on that surface. This technique of noncontact printing is particularly well suited for application of characters onto substrates such as diapers.

In general, an ink jet ink composition must meet certain rigid requirements to be useful in ink jet printing operations. These relate to viscosity and resistivity of the ink, the solubility and compatibility of the components, and the wettability of the substrate. Further, the ink must be quick drying and smear resistant, and be capable of passing through the ink jet nozzle(s) without clogging, and permit rapid cleanup of the machine components with minimum effort. The printed message in many circumstances should resist abrasion.

Preferably, the ink composition should have short dry times when printed on fabrics, e.g., porous films, used as the outer liner of the diaper. In addition, it is preferred that the ink composition be suitable for printing in a binary array print head, which may have hundreds of nozzles. Further, the printed message should preferably dissolve (disperse or be removable) rapidly when contacted with a body fluid.

Although ink jet ink compositions have been proposed for printing on diapers for wetness indication, these compositions have one or more drawbacks. For example, they have long ink dry times, the printed messages do not remove rapidly when contacted with urine, or the quality of the printed messages is poor, for example, due to the formation of so-called "micro-satellites" or mist.

The foregoing shows that there exists a need for an ink jet ink composition for printing messages on diapers for wetness indication.

The invention provides such a composition. The advantages of the invention, as well as additional inventive features, will be apparent from the description of the invention provided herein.

BRIEF SUMMARY OF THE INVENTION

The invention provides an ink composition that is suitable for ink jet printing and comprising an organic solvent, a water-soluble resin, a water-soluble dye, and optionally a surfactant. In a preferred embodiment, the organic solvent is methanol. In another embodiment, the organic solvent has a boiling point less than 78° C. The ink composition is free or substantially free of water. The printed message washes out or dissolves rapidly when contacted with an aqueous body fluid such as urine and provides an indication of the wetness. The present invention also provides a method for ink jet printing.

DETAILED DESCRIPTION OF THE INVENTION

The foregoing need has been fulfilled to a great extent by the present invention, which provides, in an embodiment, an ink composition which is suitable for ink jet printing and comprising an organic solvent, a water-soluble resin, and a water-soluble dye, wherein, if water is present, it is present in an amount less than 50% by weight of the ink composition.

In general, the ink compositions of the present invention exhibit the following characteristics for use in continuous ink jet printing systems: (1) a viscosity from about 1.6 to about 10 centipoises (cps) at 25° C.; (2) an electrical resistivity from about 50 to about 2000 ohm-cm; and (3) a sonic velocity from about 1100 to about 1700 meters/second.

Any suitable organic solvent, for example, alcohols, ketones, esters, ethers, amides, and/or lactones, can be used, with alcohol being preferred. Polar solvents are preferred. The organic solvent is preferably a low boiling solvent such as a solvent having a boiling point below 78° C. Methanol is a preferred organic solvent. The organic solvent can be present in any suitable amount, for example, in an amount of from about 50% to about 90% by weight of the ink composition, preferably in an amount of from about 55% to about 85%, and more preferably in an amount of from about 60% to about 80% by weight of the ink composition.

The ink composition is free or substantially free of water. If water is present, it is present in an amount of less than 50% by weight of the ink composition, preferably less than about 30% by weight, and more preferably less than about 15% by weight, and even more preferably less than about 10% by weight, of the ink composition. Water tends to increase ink dry time.

Any suitable water-soluble resin, for example, a resin having high water solubility, can be used. In embodiments, the water-soluble resin has a solubility of 100 g/L or more, preferably 200 g/L or more, and more preferably 500 g/L or more, in water at 37° C. The water-soluble resin acts as a binder and causes the dye to adhere to the substrate. The high water solubility of the resin facilitates removal of the printed message when contacted with urine or other aqueous fluid. In an embodiment, the water-soluble resin is also soluble in the organic solvent of the ink composition.

Any suitable water-soluble resin can be employed, for example, a polyamide, a cellulose derivative, an acrylic polymer such as an acrylic acid or acrylamide polymer, or a polyol, e.g., a water-soluble resin selected from the group consisting of polyvinylpyrrolidone, polyvinylalcohol, carboxymethylcellulose, and poly(2-ethyl-2-oxazoline), polymers (homopolymers and copolymers) based on acrylic acid, polymers (homopolymers and copolymers) based on methacrylic acid, and polymers (homopolymers and copolymers) based on acrylamide, and any combination thereof. A preferred water-soluble resin is polyvinylpyrrolidone., e.g., PVP K-15 available from ISP. Poly(2-ethyl-2-oxazoline) is available as AQUAZOL™ (preferably AQUAZOL 5) from Polymer Chemistry Innovations, Inc. in Tucson, Ariz.

The water-soluble resin can be of any suitable molecular weight, for example, a weight average molecular weight of from about 2,000 to about 30,000, and preferably from about 5000 to about 15,000. The ink jet ink composition of the present invention has an advantage in that it produces only a small amount of micro-satellites, which are believed to be due to non-uniform charging of the ink droplets. Micro-satellites or misting (of droplets) accumulate over the printer charge plates and affect the print quality as well as interfere with the continuous operation of the printer. Micro-satellite formation could be particularly significant in a binary array printer. In an embodiment, misting can be reduced by the use of low molecular weight water-soluble resins, for example, polyvinylpyrrolidone of weight average molecular weight of from about 5,000 to about 15,000.

The ink composition includes a suitable water-soluble dye, for example, a water-soluble dye selected from the group consisting of FD&C Blue No. 1, FD&C Blue No. 2, FD&C Green No. 3, FD&C Red No. 40, C.I. Food Blue 5, and C.I. Food Red 7, and any combination thereof. Preferably, the dye is soluble in the organic solvent also. In embodiments, the dye has a solubility of 50 g/L or more, preferably 100 g/L or more, and more preferably 150 g/L or more, in water at 25° C. The dye can be present in the ink composition in any suitable amount, for example, in an amount of from about 0.5 to about 10%, preferably in an amount of from about 1 to about 5%, and more preferably in an amount of from about 1.5 to about 3.5% by weight of the ink composition.

The ink composition of the present invention preferably includes one or more surfactants. Any suitable surfactant can be used; for example, a surfactant selected from the group consisting of anionic surfactants, cationic surfactants, non-ionic surfactants, and amphoteric surfactants, and any combination thereof. In an embodiment, an anionic surfactant is used. An example of a specific surfactant is diethylhexyl sodium sulfosuccinate, available as MONOWET™ MO-E75 from Uniqema, ICI. Another example of a suitable surfactant is 4-(1-aminoethyl) phenol propoxylate. Further examples of surfactants include polyoxyethylene fatty ethers, polyoxyethylene sorbitan esters, and polyoxyethylene fatty acid esters. The surfactant can be present in any suitable amount, for example, from about 0.1 to about 5%, preferably from about 0.5 to about 4%, and more preferably from about 1 to about 3% by weight of the ink composition.

The surfactant is advantageous for use in the ink composition of the present invention. In porous substrates, the dye (of the printed message) is typically found on the surface of the substrate as well as in the interior of the pores. When water or urine (or other aqueous body fluid) contacts the printed message containing a surfactant, the surfactant facilitates the dissolution and removal of the dye present in the pores. It is believed, without wishing to be bound by any theory or mechanism, that the surfactant facilitates dye removal from porous substrates by lowering the interfacial tension between the porous substrate and the liquid. It is believed that the surfactant also improves the uniformity of the ink droplets during ink jet printing. The surfactant also improves the deposition of ink droplets; it reduces ink spreading or bleeding on porous substrates.

The ink jet ink composition of the present invention is suitable for printing on substrates which have been surface treated, e.g., corona treated, or untreated.

In an embodiment, the present invention provides an ink composition which is suitable for ink jet printing and comprising an organic solvent having a boiling point less than 78° C., a water-soluble resin which is also soluble in the organic solvent, and a water-soluble dye which is also soluble in the organic solvent, wherein, if water is present, it is present in an amount less than 50% by weight, preferably less than about 30% by weight, and more preferably less than about 15% by weight, and even more preferably less than about 10% by weight, of the ink composition. The ink composition is free or substantially free of ethanol. If ethanol is present, it is present in an amount less than 15%, preferably less than 10%, and more preferably in an amount less than 5% by weight of the ink composition.

In another embodiment, the present invention provides an ink composition which is suitable for ink jet printing and comprising an organic solvent, a water-soluble resin which is also soluble in the organic solvent, and a water-soluble dye which is also soluble in the organic solvent, wherein, if water is present, it is present in an amount less than 50% by weight, preferably less than about 30% by weight, and more preferably less than about 15% by weight, and even more preferably less than about 10% by weight, of the ink composition. The ink composition is free or substantially free of ethanol. If ethanol is present, it is present in an amount less than 15%, preferably less than 10%, and more preferably in an amount less than 5% by weight of the ink composition.

In an embodiment, the ink composition of the present invention includes the organic solvent, e.g., methanol, in an amount of from about 50 to about 90% by weight, the water-soluble resin in an amount of from about 10 to about 35% by weight, the water-soluble dye in an amount of from about 0.5 to about 5% by weight, and the surfactant in an amount of from about 0.1 to about 5% by weight, of the ink composition. In a preferred embodiment, the ink composition of the present invention includes the organic solvent, e.g., methanol, in an amount of from about 60 to about 80% by weight, the water-soluble resin in an amount of from about 10 to about 30% by weight, the water-soluble dye in an amount of from about 1 to about 5% by weight, and the surfactant in an amount of from about 0.5 to about 4% by weight, of the ink composition.

The ink composition can be applied through any suitable ink jet printer, e.g., a printer employing a single or dual nozzle print head, or preferably in a printer employing a binary array print head, which provides high printing speeds and increased graphics resolution.

The present invention further provides a method for ink jet printing onto a substrate comprising projecting a stream of ink droplets to the substrate and controlling the direction of the ink droplets so that the droplets form the desired printed image on the substrate, wherein the ink droplets are formed from embodiments of the ink composition of the present invention.

The ink jet ink composition of the present invention can be applied on any suitable substrate, e.g., a fabric such as a polyolefin fabric, typically a polyethylene or polypropylene fabric. The substrate can be porous or non-porous, woven or non-woven. Porous fabrics are advantageous as they provide breathability and wearing comfort.

The invention can be applied to all types of diaper or similar absorbent materials and to form any desired image on the diaper or similar absorbent materials. Thus, for example, the invention can be used in connection with ink jet printing on incontinence pads, as well as in connection with ink jet printing on diapers for infants and training pants for older children. The term "diaper" is therefore used herein to denote in general a composite construction comprising a liquid impervious layer having in association therewith a fluid absorbent layer adapted to be in contact directly or indirectly with a wearer of the diaper, the construction being in sheet, strip or pad form and intended for use upon the person. The term "diaper fabric" is used herein to denote this construction prior to cutting or otherwise forming the individual diapers therefrom.

The ink jet ink composition of the present invention has short dry times, for example, a dry time of less than 10 seconds, preferably from about 1 to about 8 seconds, more preferably from about 1 to about 2 seconds, at a temperature of 25° C., and a relative humidity of 30-70%, image pixel density of one to two drops per pixel, and a droplet size of about 1 nanoliter. The ink jet ink composition, in embodiments, offers a dry time of from about 1 to about 2 seconds, and in certain embodiments, a dry time of from about 3 to about 4 seconds, and in certain other embodiments, a dry time of from about 7 to about 8 seconds, when messages are printed on calcium carbonate filled polyethylene fabrics using a 66 micron nozzle, at the above temperature, relative humidity, image pixel density, and droplet size.

The ink jet ink composition of the present invention prints messages on porous as well as non-porous substrates such that the messages can be removed upon contact with aqueous fluids such as urine. Accordingly, wetness indication in such diapers is rapid. The removal efficiency can be determined by any suitable method. For example, the printed substrate can be immersed in a test fluid, e.g., water, for a predetermined period of time and the residual color on the substrate can be measured. The residual color can be measured by colorimetry based on the L*, a*, b*, and c* values, and $\Delta_E$.

The present invention further provides a method for ink jet printing on a diaper which is fabricated from component materials as a composite construction comprising a substantially fluid impervious layer having in association therewith a fluid absorbent layer adapted to be in operative contact with a wearer of the diaper, which method comprises applying droplets of an ink composition to a selected one of the component materials thereof, the ink composition being applied by an ink jet printing technique which applies discrete droplets of the ink composition through at least one nozzle orifice to individually selected positions on the selected component material so as to form a desired image on the selected component of the diaper, wherein the ink composition comprises methanol, a water-soluble resin, a water-soluble dye, and optionally a surfactant. Details of assembling the various components of the diaper can be found in the literature, e.g., U.S. Pat. No. 4,909,879, the disclosure of which is incorporated by reference in its entirety.

The present invention further provides an improvement in a process for ink jet printing on a diaper fabric having a composite construction comprising a substantially fluid impervious layer formed from a polymeric material such as a polyethylene material and having in association therewith a fluid absorbent layer formed from a cellulosic fibrous material which fabric is subsequently to be formed into a diaper adapted to be worn upon the person with the absorbent layer being in operative contact with the person so as to absorb body fluids therefrom, which process comprises continuously feeding the elements of the composite fabric to a process in which they are unified into the composite fabric. The improvement comprises forming an image from a series of dots on that face of the polymeric material to be in operative contact with the absorbent layer by applying thereto an ink composition by an ink jet printer located intermediate the feed of the material and its incorporation into the composite fabric, and further comprising varying the image formed on the face of the polymeric material by varying the arrangement of the series of dots being applied by the ink jet printer while continuing to feed the elements of composite fabric to the process, wherein the ink composition comprises methanol, a water-soluble resin, a water-soluble dye, and optionally a surfactant.

The present invention further provides a method for ink jet printing on a diaper fabric having a composite construction which includes a substantially fluid impervious layer formed from a synthetic resilient sheet material having opposed faces and having in association therewith a fluid absorbent layer formed from a cellulosic fibrous material, which fabric is subsequently to be formed into a diaper adapted to be worn upon the person with the absorbent layer being contactable with the person so as to absorb body fluids therefrom, which method comprises feeding the components of the composite fabric to a process in which they are unified into the composite fabric, and forming an image on a selected one of the components by applying droplets of an ink composition to selected positions on the selected component by an ink jet printer which applies discrete droplets of the ink composition through at least one nozzle orifice to an individually selected position on the component so as to form a desired image on the component as the component is fed to the unification process, wherein the ink composition comprises methanol, a water-soluble resin, a water-soluble dye, and optionally a surfactant.

The following examples further illustrate the invention but, of course, should not be construed as in any way limiting its scope.

EXAMPLE 1

This example illustrates ink jet ink compositions in accordance with an embodiment of the present invention. The following ink compositions were prepared.

| Ingredients | Control | Ink 1 |
| --- | --- | --- |
| Methanol | 71.57% | 69.4% |
| PVP K-15 | 25.98% | 25.2% |
| FD&C Blue #1 | 2.45% | 2.4% |
| MONOWET MO-70E | — | 3.0% |
| Total | 100.00% | 100.00% |

The ink compositions were tested for removal from various polyethylene films; these films had varying degrees of porosity. Draw downs of the ink compositions were made on the films. The ink was allowed to dry and set for an hour an ambient temperature. Percentage removal when contacted with 37° C. water for 30 seconds is as follows:

|        | Control | Ink 1  |
|--------|---------|--------|
| Film 1 | 96.2%   | 96.1%  |
| Film 2 | 86.9%   | 92.6%  |
| Film 3 | 27.3%   | 80.0%  |
| Film 4 | 32.7%   | 79.8%  |

The foregoing shows an advantage of an embodiment of the present invention that the message is removed with high efficiency if a surfactant is present in the ink composition.

EXAMPLE 2

This example demonstrates additional embodiments of the ink composition whose printed messages are removable when contacted with water. Five ink jet ink compositions were prepared from ingredients shown below. Messages were printed on four different films (1-4) of differing porosity. After the printed messages were dry, the films were immersed in 37° C. tap water for 30 seconds. The amount of residual color was determined by colorimetry. The results obtained are set forth below.

Composition E was further tested for 2 minutes water immersion at 37° C.

|                | Film 3 | Film 4 |
|----------------|--------|--------|
| ΔE Before Wash | 62.5   | 63.3   |
| ΔE After Wash  | 1.1    | 2.2    |
| % Removal      | 98.2%  | 96.5%  |

The foregoing shows that embodiments of the ink composition of the present invention print messages that can be removed upon contact with water.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and

| | Compositions weight % | | | | |
|---|---|---|---|---|---|
| | A | B | C | D | E |
| Methanol | 77.12 | 74.00 | 79.70 | 64.75 | 74.81 |
| PVP K-15 | 20.91 | 20.10 | | | 20.28 |
| AQUAZOL 5 | | | 14.30 | | |
| KOLLIDON 12 PF (PVP K-12) | | | | 29.25 | |
| FD&C Blue #1 | 1.97 | 1.90 | 2.00 | 2.00 | 1.91 |
| MONAWET MO-70E | | 3.00 | 3.00 | 3.00 | 3.00 |
| 4-(1-Aminoethyl)phenol propoxylate | | 1.00 | 1.00 | 1.00 | |

| | A | B | C | D | E |
|---|---|---|---|---|---|
| Film 1 | | | | | |
| ΔE (before wash/blank) | 50.4 | 67.4 | 68.2 | 61.6 | 69.2 |
| ΔE (before/after wash) | 43.8 | 65.6 | 67.8 | 61.6 | 68.7 |
| ΔE (after wash/blank) | 7.1 | 1.8 | 0.5 | 0.9 | 0.6 |
| % Removal | 86.9% | 97.4% | 99.5% | 99.9% | 99.2% |
| Film 2 | | | | | |
| ΔE (before wash/blank) | 50.4 | 58.1 | 59.6 | 61.8 | 62.3 |
| ΔE (before/after wash) | 43.8 | 53.7 | 58.1 | 57.2 | 61.0 |
| ΔE (after wash/blank) | 7.1 | 5.1 | 2.7 | 5.0 | 1.6 |
| % Removal | 86.9% | 92.6% | 97.6% | 92.6% | 97.9% |
| Film 3 | | | | | |
| ΔE (before wash/blank) | 51.1 | 52.2 | 57.9 | 56.1 | 59.5 |
| ΔE (before/after wash) | 13.9 | 45.2 | 50.0 | 37.1 | 51.9 |
| ΔE (after wash/blank) | 37.2 | 8.7 | 9.1 | 20.4 | 8.4 |
| % Removal | 27.3% | 86.5% | 86.4% | 66.2% | 87.2% |
| Film 4 | | | | | |
| ΔE (before wash/blank) | 48.2 | 55.2 | 58.2 | 59.2 | 59.1 |
| ΔE (before/after wash) | 25.8 | 46.1 | 49.1 | 45.4 | 51.3 |
| ΔE (after wash/blank) | 23.3 | 10.0 | 10.0 | 14.9 | 9.6 |
| % Removal | 53.7% | 83.4% | 84.2% | 76.7% | 86.8% |

"containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An ink composition which is suitable for ink jet printing and comprising methanol, polyvinylpyrrolidone, a water-soluble dye, and a surfactant, wherein, if water is present, it is present in an amount less than 10% by weight of the ink composition.

2. An ink composition which is suitable for ink jet printing and comprising methanol, a water-soluble resin, a water-soluble dye, and a surfactant, wherein if water is present, it is present in an amount less than 10% by weight of the ink composition, wherein the water-soluble resin is selected from the group consisting of polyvinylalcohol, carboxymethylcellulose, poly(2-ethyl-2-oxazoline), and polymers based on acrylamide, and any combination thereof.

3. The ink composition of claim 1, wherein the polyvinylpyrrolidone has a weight average molecular weight of from about 2,000 to about 30,000.

4. The ink composition of claim 3, wherein the polyvinylpyrrolidone has a weight average molecular weight of about 5,000 to about 15,000.

5. The ink composition of claim 1, wherein the water-soluble dye is selected from the group consisting of FD&C Blue No. 1, FD&C Blue No. 2, FD&C Green No. 3, FD&C Red No. 40, C.I. Food Blue 5, and C.I. Food Red 7, and any combination thereof.

6. The ink composition of claim 1, which is free or substantially free of water.

7. The ink composition of claim 1, wherein the surfactant is selected from the group consisting of anionic surfactants, cationic surfactants, nonionic surfactants, and amphoteric surfactants, and any combination thereof.

8. An ink composition which is suitable for ink jet printing and comprising methanol, a water-soluble resin, a water-soluble dye, and a surfactant, wherein, if water is present, it is present in an amount less than 50% by weight of the ink composition, wherein the surfactant is diethylhexyl sodium sulfosuccinate.

9. The ink composition of claim 1, which includes water, wherein water is present in an amount less than 10% by weight of the ink composition.

10. The ink composition of claim 1, wherein methanol is present in an amount of from about 50 to about 90% by weight, the polyvinylpyrrolidone is present in an amount of from about 10 to about 35% by weight, the water-soluble dye is present in an amount of from about 0.5 to about 5% by weight, and the surfactant is present in an amount of from about 0.1 to about 5% by weight, of the ink composition.

11. An ink composition which is suitable for ink jet printing and comprising methanol, polyvinylpyrrolidone, and a water-soluble dye, wherein, if water is present, it is present in an amount less than 10% by weight of the ink composition.

12. An ink composition which is suitable for ink jet printing and comprising an organic solvent having a boiling point less than 78° C., polyvinylpyrrolidone, and a water-soluble dye which is also soluble in the organic solvent, wherein, if water is present, it is present in an amount less than 10% by weight of the ink composition.

13. An ink composition which is suitable for ink jet printing and comprising an organic solvent, polyvinylpyrrolidone, and a water-soluble dye which is also soluble in the organic solvent, wherein, if water is present, it is present in an amount less than 10% by weight of the ink composition, and the ink composition is free or substantially free of ethanol.

14. The ink composition of claim 12, wherein the organic solvent is methanol.

15. The ink composition of claim 13, wherein the organic solvent is methanol.

16. A method for ink jet printing on a diaper which is fabricated from component materials as a composite construction comprising a substantially fluid impervious layer having in association therewith a fluid absorbent layer adapted to be in operative contact with a wearer of the diaper, which method comprises applying droplets of an ink composition to a selected one of the component materials thereof, the ink composition being applied by an ink jet printing technique which applies discrete droplets of the ink composition through at least one nozzle orifice to individually selected positions on the selected component material so as to form a desired image on the selected component of the diaper, wherein the ink composition comprises methanol, polyvinylpyrrolidone, a water-soluble dye, and optionally a surfactant, and wherein if water is present, it is present in an amount less than 10% by weight of the ink composition.

17. In a process for ink jet printing on a diaper fabric having a composite construction comprising a substantially fluid impervious layer formed from a polymeric material and having in association therewith a fluid absorbent layer formed from a cellulosic fibrous material which fabric is subsequently to be formed into a diaper adapted to be worn upon the person with said absorbent layer being in operative contact with the person so as to absorb body fluids therefrom, which process comprises continuously feeding the elements of the composite fabric to a process in which they are unified into the composite fabric, the improvement which comprises forming an image from a series of dots on that face of the polymeric material to be in operative contact with said absorbent layer by applying thereto an ink composition by an ink jet printer located intermediate the feed of said material and its incorporation into the composite fabric, and further comprising varying the image formed on the face of the polymeric material by varying the arrangement of the series of dots being applied by the ink jet printer while continuing to feed the elements of composite fabric to the process, wherein the ink composition comprises methanol, polyvinylpyrrolidone, a water-soluble dye, and optionally a surfactant, and wherein if water is present, it is present in an amount less than 10% by weight of the ink composition.

18. A method for ink jet printing on a diaper fabric having a composite construction which includes a substantially fluid impervious layer formed from a synthetic resilient sheet material having opposed faces and having in association therewith a fluid absorbent layer formed from a cellulosic fibrous material, which fabric is subsequently to be formed into a diaper adapted to be worn upon the person with said absorbent layer being contactable with the person so as to absorb body fluids therefrom, which method comprises feeding the components of the composite fabric to a process in which they are unified into the composite fabric, and forming an image on a selected one of said components by applying droplets of an ink composition to selected positions on said selected component by an ink jet printer which applies discrete droplets of the ink composition through at least one nozzle orifice to an individually selected position on said component so as to form a desired image on said component as said component is fed to the unification process, wherein the ink composition comprises methanol, polyvinylpyrrolidone, a water-soluble dye, and optionally a surfactant, and wherein if water is present, it is present in an amount less than 10% by weight of the ink composition.

19. The method of claim 16, wherein the ink composition is applied through a binary array print head.

20. A method for ink jet printing onto a substrate comprising projecting a stream of ink droplets to said substrate and controlling the direction of said ink droplets so that the droplets form the desired printed image on the substrate, wherein said ink droplets are formed from the ink composition of claim 1.

21. A method for ink jet printing onto a substrate comprising projecting a stream of ink droplets to said substrate and controlling the direction of said ink droplets so that the droplets form the desired printed image on the substrate, wherein said ink droplets are formed from the ink composition of claim 11.

22. A method for ink jet printing onto a substrate comprising projecting a stream of ink droplets to said substrate and controlling the direction of said ink droplets so that the droplets form the desired printed image on the substrate, wherein said ink droplets are formed from the ink composition of claim 12.

23. A method for ink jet printing onto a substrate comprising projecting a stream of ink droplets to said substrate and controlling the direction of said ink droplets so that the droplets form the desired printed image on the substrate, wherein said ink droplets are formed from the ink composition of claim 13.

24. The method of claim 20, wherein the substrate is a fabric.

25. The method of claim 24, wherein the fabric is porous.

26. An ink composition which is suitable for ink jet printing and comprising methanol, polyvinylpyrrolidone, and a water-soluble dye, wherein the ink composition is free or substantially free of water.

27. The ink composition of claim 26, which further includes a surfactant.

28. The ink composition of claim 26, wherein the polyvinylpyrrolidone has a weight average molecular weight of from about 2,000 to about 30,000.

29. The ink composition of claim 26, wherein the water-soluble dye is selected from the group consisting of FD&C Blue No. 1, FD&C Blue No. 2, FD&C Green No. 3, FD&C Red No. 40, C.I. Food Blue 5, and C.I. Food Red 7, and any combination thereof.

* * * * *

UNITED STATES PATENT AND TRADEMARK OFFICE
CERTIFICATE OF CORRECTION

| | | |
|---|---|---|
| PATENT NO. | : 7,285,160 B2 | Page 1 of 1 |
| APPLICATION NO. | : 10/701733 | |
| DATED | : October 23, 2007 | |
| INVENTOR(S) | : Linfang Zhu, James D. McClellan and John P. Folkers | |

It is certified that error appears in the above-identified patent and that said Letters Patent is hereby corrected as shown below:

Detailed Description of the Invention, Column 3, Lines 44 and 45: "MONOWET™ MO-E75" should read --MONAWET™ MO-70E--

Example 1, Column 6, Line 57: "MONOWET MO-70E" should read --MONAWET MO-70E--

Signed and Sealed this

Eleventh Day of March, 2008

JON W. DUDAS
*Director of the United States Patent and Trademark Office*